United States Patent
Iwami et al.

(10) Patent No.: US 6,811,958 B2
(45) Date of Patent: Nov. 2, 2004

(54) MEDICAL LONG OBJECT AND METHOD FOR PRODUCING THE SAME

(75) Inventors: Jun Iwami, Shizuoka (JP); Hideki Fujimagari, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 48 days.

(21) Appl. No.: 09/984,611

(22) Filed: Oct. 30, 2001

(65) Prior Publication Data

US 2002/0087098 A1 Jul. 4, 2002

(30) Foreign Application Priority Data

Oct. 30, 2000 (JP) ........................................ 2000-330522

(51) Int. Cl.⁷ ............................ A61B 5/00; A61M 25/09
(52) U.S. Cl. ........................ 430/320; 430/346; 430/945; 600/585; 600/433; 600/434; 600/435; 604/164.1; 604/264; 604/171
(58) Field of Search ................................. 430/320, 346, 430/945; 600/585, 433, 434, 435; 604/164.01, 264, 171

(56) References Cited

U.S. PATENT DOCUMENTS

| | | | |
|---|---|---|---|
| 4,951,686 A | | 8/1990 | Herlitze |
| 5,084,022 A | * | 1/1992 | Claude .................. 604/164.13 |
| 5,379,779 A | | 1/1995 | Rowland et al. |
| 5,454,881 A | | 10/1995 | Fischer |
| 5,811,369 A | * | 9/1998 | Nagai et al. ................. 503/209 |
| 5,919,170 A | * | 7/1999 | Woessner .................... 604/264 |
| 6,022,905 A | * | 2/2000 | Harris et al. .................... 522/2 |
| 6,520,951 B1 | * | 2/2003 | Carrillo et al. ............. 604/516 |

FOREIGN PATENT DOCUMENTS

| | | |
|---|---|---|
| EP | 0 519 214 A1 | 12/1992 |
| EP | 0 669 365 A1 | 8/1995 |
| JP | 4-108556 U | 9/1992 |
| JP | 6-63054 U | 9/1994 |
| WO | 94/01160 A1 | 1/1994 |
| WO | WO 95/05574 A2 | 2/1995 |

OTHER PUBLICATIONS

Bosnos, Chuck; Burton, Natalie; McKee, Terry. "Laser Marking Medical Devices and Packaging". Feb. 1998. www.devicelink.com/mddi/archive/98/02/018.html.*

J. Mvers, "Lasers Make Their Mark on Variety of Plastics Parts," *Modern Plastics International*, vol. 23, No. 10, Oct. 1993, pp. 29–31.

* cited by examiner

*Primary Examiner*—John A. McPherson
(74) *Attorney, Agent, or Firm*—Burns, Doane, Swecker & Mathis, L.L.P.

(57) ABSTRACT

A medical long object of the present invention has a part made of a polymeric material containing a laser color developing agent at least in a part of the surface thereof, and a light developing portion formed in the part by color development of the laser color developing agent due to irradiation with laser light.

3 Claims, 2 Drawing Sheets

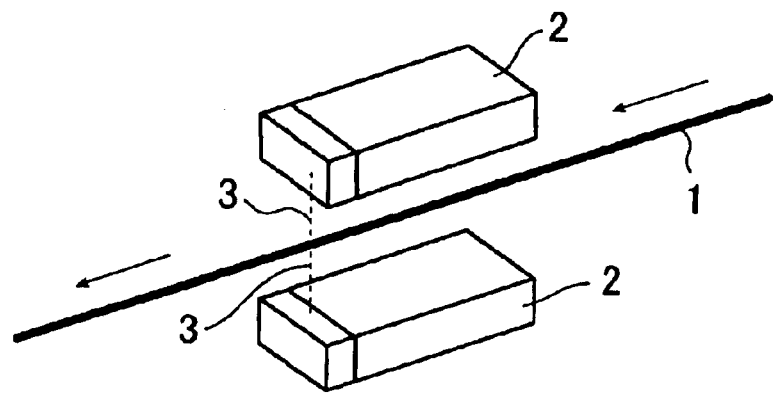
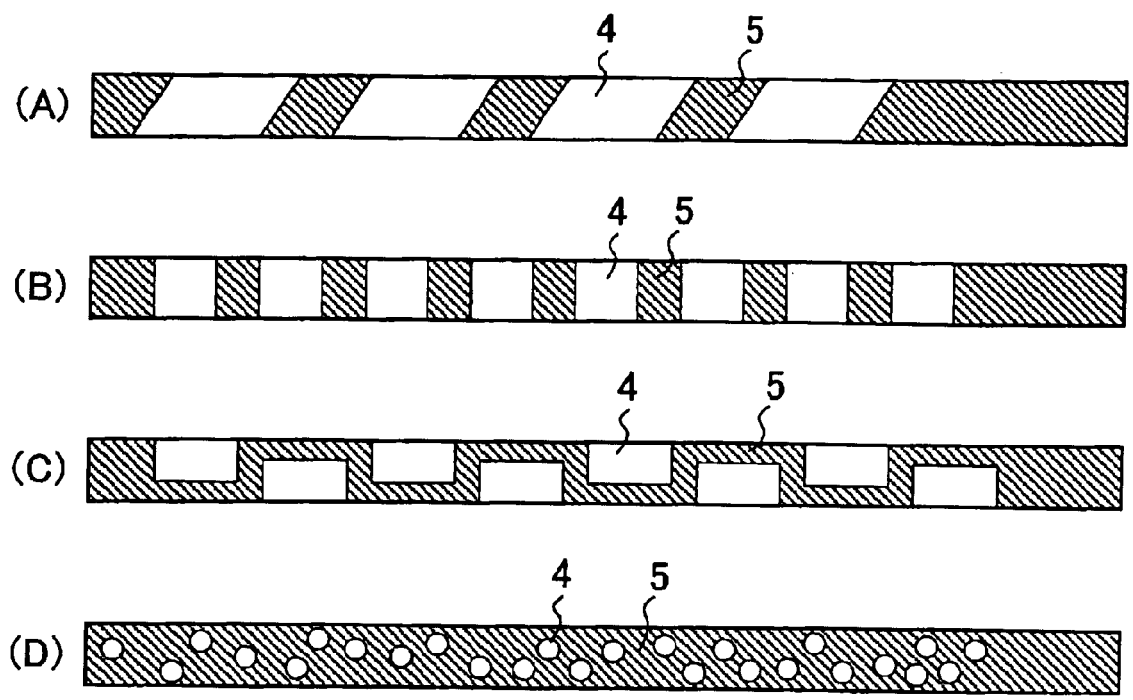

MEDICAL LONG OBJECT AND METHOD FOR PRODUCING THE SAME

BACKGROUND OF THE INVENTION

1. Field of the Invention

The present invention relates to a medical long object having a mark on its surface.

2. Description of the Related Art

In observation of a biological lumen or the like using an endoscope, in order to guide the endoscope to a predetermined position of the biological lumen or the like, a guide wire is used. The guide wire is inserted to the predetermined position of the biological lumen or the like before guiding the endoscope.

If the guide wire is monochromic, the movement thereof is not recognized even when it is moving in an axial direction. Therefore, it is preferable that a mark representing a position and the like of the guide wire is provided on the surface thereof.

Therefore, conventionally, a method for providing various marks has been proposed.

For example, JP 09-501593 A discloses a method for attaching a hollow tube to a guide wire. According to this method, a hollow tube made of Teflon or the like and having a plurality of colored streaks is shrunk over a core wire of a guide wire so as to wrap it.

In the above-mentioned method, a mark is provided simultaneously with the formation of the guide wire. Therefore, it is difficult to provide a mark at a desired position. Furthermore, the shape and width of a mark may become uniform as a whole.

JP 04-108556 U discloses a method for forming a mark by printing.

The above-mentioned method has the following problems. Since ink has no solvent resistance, it is difficult to provide a lubricating coat such as a hydrophilic polymer to the surface of a guide wire after forming a mark. It is also difficult to conduct marking on a curved surface. A time for drying ink is also required. During use, ink may peel off to flow into a living body.

In order to solve the problems of the above-mentioned method using printing, JP 06-63054 U discloses a method for providing a transparent coating layer made of fluorine resin after printing a mark.

According to this method, a process of drying ink is required, which complicates production processes. Furthermore, there is a constraint in terms of design that transparent resin can only be used.

Furthermore, U.S. Pat. No. 4,951,686 discloses a method for heating a site of a catheter guide wire made of steel, in which a color mark is to be formed, at a temperature allowing a temper color to appear.

According to this method, only a catheter guide wire made of steel can be used. Furthermore, a superelastic alloy (Ni-Ti alloy) generally used as a core wire of a guide wire is likely to have its physical properties changed by heat treatment such as heating. Therefore, this method is not preferable.

U.S. Pat. No. 4,951,686 also discloses a method for forming marks by stamping or irradiation with laser light.

According to the former method, a mark portion to be formed may be raised, and according to the latter method, a mark portion to be formed may be recessed, and thus obtained mark is less visible since the mark has no color change.

Thus, there is a demand for a guide wire without having the above-mentioned problems.

The above-mentioned problems are not limited to guide wires. For example, in catheters, information such as a scale (length from a tip end, etc.) is printed on a surface. Therefore, the catheters also have the same problems as those in the guide wires.

SUMMARY OF THE INVENTION

Therefore, with the foregoing in mind, it is an object of the present invention to provide a medical long object which has a mark with any shape and width at a desired position on its surface and is excellent in solvent resistance, and in which a mark position can be curved, there is no possibility of peeling of a mark during use, various materials such as a superelastic alloy (Ni-Ti alloy) can be used as a core wire, and a mark is easily visible since it has little raised or recessed.

Furthermore, it is another object of the present invention to provide a method for producing a medical long object, in which a time for drying ink is not required, and production processes are not complicated.

More specifically, the present invention provides a medical long object including a part formed of a polymeric material containing a laser color developing agent at least in a part of a surface, and a color developing portion formed in the part by color development of the laser color developing agent due to irradiation with laser light.

In particular, the present invention provides a medical long object having a tip end portion and a base end portion, including a polymeric material surface formed of a polymeric material containing a laser color developing agent at least in the tip end portion, and a light developing portion formed by color development of the laser color developing agent due to irradiation with laser light on the polymeric material surface.

It is preferable that the laser color developing agent contains mica and/or a compound thereof.

In one preferred embodiment of the present invention, the above-mentioned medical long object is a guide wire.

In one preferred embodiment of the present invention, the above-mentioned medical long object is a catheter.

Furthermore, the present invention provides a method for producing a medical long object, including: forming at least a part of a surface of a medical long object with a polymeric material containing a laser color developing agent; and irradiating only a portion of the surface of the medical long object in which a color is to be developed with laser light so as to allow the laser color developing agent to develop a color, thereby forming any pattern on the surface of the medical long object.

It is preferable that the laser color developing agent is contained 0.01 to 10% by mass on the total amount of the polymeric material component.

These and other advantages of the present invention will become apparent to those skilled in the art upon reading and understanding the following detailed description with reference to the accompanying figures.

BRIEF DESCRIPTION OF THE DRAWINGS

In the accompanying drawings:

FIG. 1 is a conceptual diagram showing an example of a method for irradiating laser light in production of a guide wire that is a medical long object of the present invention;

FIGS. 2A to 2D show specific examples of a pattern on the surface of each guide wire.

DETAILED DESCRIPTION OF THE PREFERRED EMBODIMENTS

Figure 3:
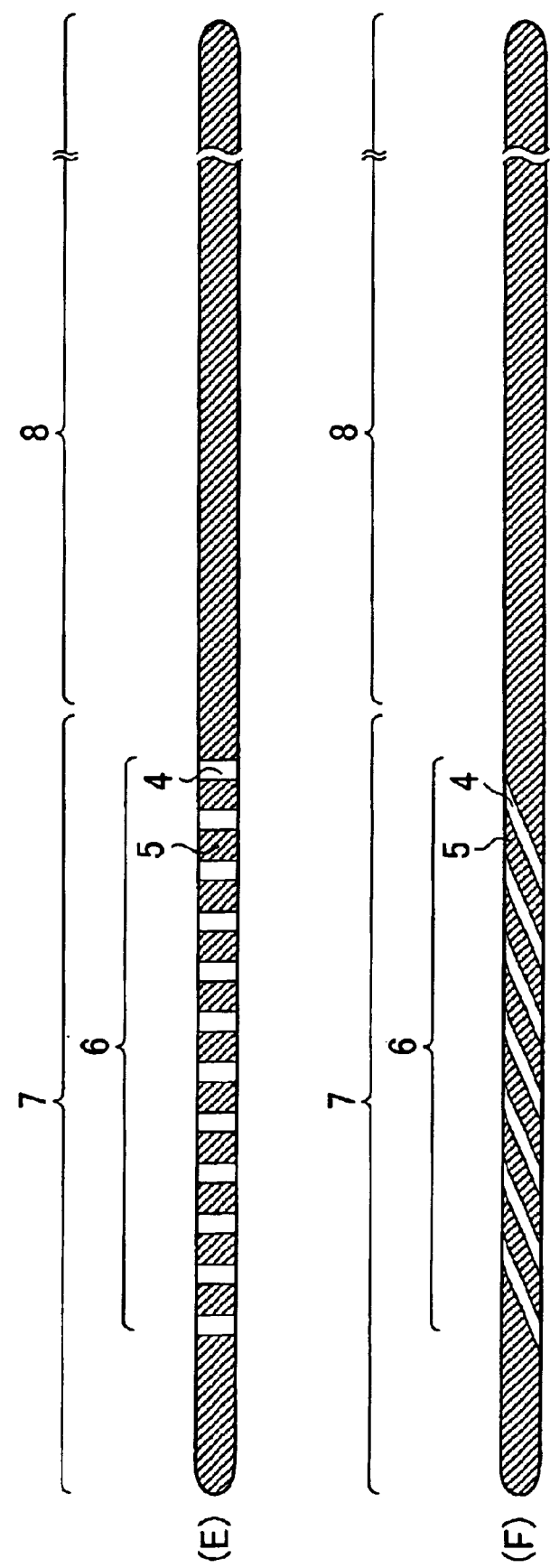
FIGS. 3E and 3F are plan views of medical long objects (guide wires) produced in Example 3.

Hereinafter, the present invention will be described in detail with reference to the drawings.

A medical long object of the present invention has a part made of a polymeric material containing a laser color developing agent at least in a part of its surface.

Examples of a polymeric material used in the present invention include resin, rubber, and the like. Examples of the resin include polyurethane, polyethylene, polypropylene, an ethylene-propylene copolymer, fluorine resin (e.g., polytetrafluoroethylene), polyethylene terephthalate, polyvinyl chloride, polyamide, polyimide, an ethylene-vinyl acetate copolymer, an ethylene-ethyl acrylate copolymer, silicone, polycarbonate, a styrene-butadiene copolymer, ABS resin, polyisoprene, and polybutadiene. Of those, polyurethane is preferable.

These materials may be used alone or in combination.

There is no particular limit to a laser color developing agent used in the present invention, as long as it develops a color by irradiation with laser light. It is preferable that the laser color developing agent contains mica and/or a compound thereof. When the laser color developing agent containing mica and/or a compound thereof is used, there are the following advantages: a laser color developing agent develops a color sufficiently only by being contained in a polymeric material in a small amount, a color developing portion is hardly raised or recessed, since the content of a laser color developing agent may be small, a change in a color of a non-color developing portion can be suppressed, and the like.

Note that the term "color development" used in the present specification also includes all the perceivable changes in a color such as discoloration, decolorization, and fading in addition to color development.

Examples of the laser color developing agent containing mica and/or a compound thereof include natural mica such as mica belonging to muscovite series (e.g., muscovite, lepidolite, paragonite, sericite, roscoelite, illite), mica belonging to biotite series (e.g., biotite, phlogopite, lepidolite, zinnwaldite), glauconite, celadonite, muscovite, phlogovite, suzolite, paragonite, and vermiculite; synthetic mica (specifically, Iriodin LS-800 produced by Merck Japan Co., Ltd. having a particle diameter of 15 µm or less, Iriodin LS-805 produced by Merck Japan Co., Ltd. having a particle diameter of 2 to 100 µm); a composition (hereinafter, referred to as "Mica composition 1". More specifically, Iriodin LS-820 produced by Merck Japan Co., Ltd. having a particle diameter of 15 µm or less) composed of mica, titanium oxide, silicon oxide, and tin oxide doped with antimony oxide; a composition (hereinafter, referred to as "Mica composition 2". More specifically, Iriodin LS-825 produced by Merck Japan Co., Ltd. having a particle diameter of 15 µm or less) composed of mica and tin oxide doped with antimony oxide; a composition (hereinafter, referred to as "Mica composition 3". More specifically, Iriodin LS-810 produced by Merck Japan Co., Ltd. having a particle diameter of 2 to 28 µm) composed of mica and titanium oxide; a composition (hereinafter, referred to as "Mica composition 4". More specifically, Iriodin LS-830 produced by Merck Japan Co., Ltd. having a particle diameter of 10 to 60 µm) composed of mica, titanium oxide, and iron oxide; and a composition (hereinafter, referred to as "Mica composition 5". More specifically, Iriodin LS-835 produced by Merck Japan Co., Ltd. having a particle diameter of 15 µm or less) composed of mica and iron oxide. Of those, Mica compositions 1 and 2 are preferable.

These laser color developing agents may be used alone or in combination.

The content of the laser color developing agent in the polymeric material is varied depending upon the kind of the laser color developing agent, the color of the polymeric material, and the like. In general, the content of the laser color developing agent is preferably 0.01 to 10% by mass, more preferably 0.1 to 2% by mass based on the total amount of the polymeric material component. The color tone after irradiation with laser light can be regulated by the content of the laser color developing agent.

In the case of using Mica composition 1 and/or 2, in particular high color development can be obtained with a small content thereof. More specifically, when the mica composition is contained in the polymeric material component in an amount of 0.01 to 2% by mass, more preferably 0.1 to 1% by mass, high color development can be obtained.

Additives other than the laser color developing agent (e.g., a filler, a pigment, a dye, an antiaging agent, an antioxidant, an anti-static agent, a lubricant, a plasticizer, a thermal stabilizer, X-ray contrast medium) can be added to the polymeric material used in the present invention in such a manner as not to impair the objects of the present invention.

The medical long object of the present invention only needs to have a part made of a polymeric material containing a laser color developing agent in any part of the surface. In the case where the medical long object of the present invention has a tip end portion and a base end portion, it is one preferred embodiment that the above-mentioned part is provided at least in the tip end portion of the surface. If there is a mark in the tip end portion of the surface, it becomes easy to manipulate the medical long object, and information on the length from the tip end and the like can be displayed.

More specifically, in one preferred embodiment of the present invention, a medical long object has a tip end portion and a base end portion, the medical long object being characterized by including a polymeric material surface made of a polymeric material containing a laser color developing agent at least in the tip end portion, and has a color developing portion formed by color development of the laser color developing agent due to irradiation with laser light on the polymeric material surface.

According to the present invention, the entire surface of the medical long object or the entire medical long object may be made of a polymeric material containing the above-mentioned laser color developing agent.

In the case where only a part of the surface of the medical long object is made of a polymeric material containing a laser color developing agent, a material of the other part is not particularly limited, and appropriately selected in accordance with the use of the medical long object.

Furthermore, in order to enhance the slidability with respect to a biological lumen and the like, the surface of the medical long object of the present invention may be coated with a low-friction material, whereby the medical long object has its friction reduced and can be smoothly inserted into a biological lumen or the like, thus operability and safety thereof are enhanced.

An example of the low-friction material includes a hydrophilic polymer.

Examples of the hydrophilic polymer include natural polymeric materials (e.g., starches, celluloses, polysaccharides, protein), and synthetic polymeric materials (e.g., PVA, polyethylene oxides, acrylic acids, maleic anhydrides, phthalic acids, water-soluble polyester, (meth) acrylamides, polyamines, water-soluble nylons type). Of those, in particular, cellulose type polymeric materials (e.g., hydroxypropylcellulose), polyethylene oxide type polymeric materials (e.g., polyethylene glycol), maleic anhydride type polymeric materials (e.g., maleic anhydride copolymer such as a copolymer of methyl vinyl ether and maleic anhydride), acrylamide type polymeric materials (e.g., polydimethylacrylamide), and water-soluble nylon (e.g., AQ-nylon P-70 produced by Toray Industries, Inc.). This is because their derivatives with a low friction coefficient can be obtained stably.

In the case where the surface of the medical long object of the present invention is coated with a low-friction material, among the hydrophilic polymers described-above, those which are transparent or semi-transparent are used so that a light developing portion on the surface can be observed from outside even if being coated.

The medical long object of the present invention has, in a part made of a polymeric material containing a laser color developing agent, a color developing portion formed by color development of the laser color developing agent due to irradiation with laser light.

Laser light used for irradiation is selected in accordance with a laser color developing agent. Examples of the laser light include near-infrared laser light such as Nd-YAG laser light, near-infrared laser light such as $CO_2$ laser light, and excimer laser light.

The Nd-YAG laser light can be near-infrared ray with a wavelength of 1.06 μm, which can be obtained by irradiating a YAG (yttrium aluminum garnet) lot with light of an arc lamp.

$CO_2$ laser light is far infrared ray with a wavelength of 10.6 μm, which can be obtained by applying a high frequency (RF) and a high voltage (TEA) to a tube in which $CO_2$ mixed gas is filled, thereby exciting the $CO_2$ mixed gas.

In the case where the above-mentioned mica (those which have a particle diameter of 15 μm or less; those which have a particle diameter of 2 to 100 μm) and the above-mentioned Mica composition 3 are used as a laser color developing agent, $CO_2$ laser light among the above-mentioned laser light is preferable. In the case where the Mica compositions 1 and 2 are used, YAG laser light is preferable. In the case where the above-mentioned Mica compositions 4 and 5 are used, $CO_2$ laser light or YAG laser light are preferable.

For example, in the case of Nd-YAG laser light, the irradiation amount of laser light is preferably in a range of 1.8 to 2.0 kW as an energy output of an irradiation origin.

Laser is not particularly limited. For example, conventionally known laser such as those of scanning type, dot type, and mask type can be used.

In the scanning type, laser light emitted from an oscillator is scanned in an X-Y direction by two rotation mirrors, and then condensed with a lens, and radiated. According to this type, laser light is radiated while a medical long object is allowed to stand still, so that marking with any shape can be conducted.

In the dot type, laser light is tuned to a polygon mirror rotated at a high speed, and is radiated. High-speed marking can be conducted.

In the mask type, laser light passes through a patterned mask (stencil) and a condensing lens to be radiated. High-speed marking and marking with a fine pattern can be conducted.

These lasers can be appropriately selected in accordance with the use and the like of a medical long object.

Due to irradiation with laser light, a laser color developing agent contained in a polymeric material develops a color to form a color developing portion. Because of this, the surface of the medical long object can be provided with a mark. For example, a plurality of marks can be formed at desired positions over the length by irradiation with laser light.

Examples of a mark include a letter, a number, a pattern, a design, and the like. By selecting a laser color developing agent, a mark can be formed in monochrome or color.

The size, shape, and the like of the medical long object of the present invention can be appropriately determined in accordance with the use and purpose.

The medical long object of the present invention can be used, for example, as a guide wire and a catheter.

A guide wire and a catheter have a curved surface. Therefore, it is difficult to apply the conventional method for forming a mark to a guide wire and a catheter. Therefore, a guide wire and a catheter are included in one preferred embodiment of the medical long object of the present invention.

The case will be described where the medical long object of the present invention is a guide wire.

As long as the guide wire of the present invention has a part made of a polymeric material containing a laser color developing agent at least in a part of the surface thereof, and has a color developing portion formed in the part by color development of the laser color developing agent due to irradiation with laser light, there is no particular limit to the guide wire, and a known shape, structure, and the like can be adopted.

A core wire used in the guide wire of the present invention is a line material having flexibility. A constituent material for the core wire is not particularly limited, and various plastics and various metals can be used. However, it is preferable that the core wire is made of a superelastic alloy. Because of this, a guide wire excellent in torque transferability and kink (bending) resistance can be obtained without increasing the diameter of the guide wire.

Herein, a superelastic alloy is generally called a shape-memory alloy, which refers to an alloy exhibiting superelasticity at a service temperature. Superelasticity refers to a property of metal in which even if ordinary metal is deformed (bent, pulled, compressed) to plastic deformation at a service temperature, i.e., at least a temperature of a living body (in the vicinity of 37° C.), the metal is restored to substantially the original shape. Examples of a preferable composition of a superelastic alloy include superelastic body such as a Ti-Ni alloy containing 49 to 58% by atom of Ni, a Cu-Zn alloy containing 38.5 to 41.5% by mass of Zn, a Cu-Zn-X alloy (where X is at least one selected from Be, Si, Sn, Al, and Ga) containing 1 to 10% by mass of X, and an Ni-Al alloy containing 36 to 38% by atom of Al. Among them, the Ti-Ni alloy is preferable.

Although not particularly limited, the diameter of a core wire used in the guide wire of the present invention is preferably in a range of 0.25 to 1.57 mm, more preferably in a range of 0.4 to 0.97 mm.

It is preferable that the tip end portion of the core wire is tapered in accordance with characteristics such as touch resistance, bend resistance, and the like, and its outer diameter is gradually reduced toward the tip end. Because of this, when the guide wire is inserted into a biological lumen or the like from the tip end side so as to reach an intended site (lesion), when the guide wire can flexibly follow a complicated shape such as a curve and a branch of the biological lumen, whereby the guide wire can be easily and safely inserted into and removed from the lumen.

The guide wire of the present invention is obtained by coating at least a part of the surface of the above-mentioned core wire with a polymeric material containing a laser color developing agent.

Although the thickness of a coating layer is not particularly limited, it is preferably 0.05 to 0.3 mm on the average, more preferably 0.1 to 0.2 mm on the average.

Furthermore the thickness of the coating layer may be uniform over the entire layer or may be varied depending upon a site. For example, it may have taken structure that the thickness of the coating layer may be increased in the vicinity of the tip end portion of the guide wire.

Note that the number of coating layers is not limited to one, and a plurality of stacked coating layers may be used.

The guide wire is generally used to be inserted into and held in a living body under X-ray fluoroscopy. Therefore, it is preferable that the guide wire body is provided with an X-ray contrast property. That is, it is preferable that an X-ray contrast medium is contained in a constituent material of the guide wire body. Examples of the X-ray contrast medium include metal or a metal compound such as platinum, silver, tungsten, barium sulfate, and bismuth oxide.

The case will be described where the medical long object of the present invention is a catheter.

As long as the catheter of the present invention has a part made of a polymeric material containing a laser color developing agent at least in a part of the surface thereof, and has a color developing portion formed in the part by color development of the laser color developing agent due to irradiation with laser light, there is no particular limit to the catheter, and a known shape, structure, and the like can be adopted.

As long as the catheter of the present invention has a part made of a polymeric material containing a laser color developing agent at least in a part of the surface thereof, the other part may be made of a material with flexibility, such as polyvinyl chloride, polyurethane, polyethylene, polypropylene, polyamide, polytetrafluoroethylene, silicone rubber, and an ethylene-vinyl acetate copolymer. The polymeric material used in a part made of a polymeric material containing a laser color developing agent may be the same as or different from the polymeric material used in the other part. By appropriately selecting the above-mentioned material, the diameter of the catheter body, and the like, the tip end portion of the catheter has flexibility to such a degree as to be easily bent when pulled by a wire described later.

Furthermore, by burying or by coating a reinforcing member made of a polymeric material (e.g., hard polyurethane and polyimide) or metal (e.g., a coil spring) in a part of the catheter body except for the tip end portion, the stiffness of the part of the catheter body excluding the tip end portion can be enhanced compared with that of the tip end portion.

Note that he catheter is generally used to be inserted into and held in a living body under X-ray fluoroscopy. Therefore, it is preferable that the catheter body is provided with an X-ray contrast property. That is, it is preferable that an X-ray contrast medium is contained in a constituent material of the catheter body. Examples of the X-ray contrast medium include metal or a metal compound such as the above-mentioned platinum, silver, tungsten, barium sulfate, or bismuth oxide.

The catheter body may be provided with various lumens having different uses and functions as described below.

For example, there is a lumen in which an optical fiber bundle that functions as observation equipment (fiber scope) for observing an inside of a body cavity such as a blood vessel and a tubular organ is accommodated. Note that the optical fiber bundle can also be used for medical treatment such as irradiation with laser light to a blood vessel and an inner wall of a tubular organ.

There is also a lumen that is opened at the tip end portion of the catheter body in such a manner that fluid can be injected into a body cavity or the like through the opening or fluid can be aspired from the body cavity or the like.

Furthermore, there is a lumen for accommodating a wire for pulling the tip end of the catheter body so as to curve the tip end portion of the catheter body.

Note that one or two more expandable body such as a balloon that can be expanded by injecting an operation fluid may be disposed in the vicinity of the tip end portion of the catheter body and on the base end side from a curved point of the tip end portion. In this case, a lumen communicated with the expandable body is formed in the catheter body so as to feed the operation fluid to the expandable body.

The shape, structure, and the like of the catheter of the present invention are varied depending upon the purpose of the catheter.

For example, in the case of a epidural catheter, the outer diameter is preferably 0.6 to 1.5 mm, more preferably 0.8 to 1.2 mm, and the inner diameter is preferably 0.3 to 0.9 mm, more preferably 0.4 to 0.6 mm. Furthermore, in the case of a vascular catheter, the outer diameter is preferably 0.8 to 2.5 mm, and the inner diameter is preferably 0.3 to 2.0 mm. Furthermore, in the case of a contrast catheter, the outer diameter is preferably 2.7 mm or less, more preferably 2.0 mm or less, and the inner diameter is preferably 0.9 to 1.8 mm, more preferably 1.0 to 1.5 mm. By prescribing the inner diameter and the outer diameter in such a range, the catheter can sufficiently exhibit flexibility and a following property with respect to a curve.

Furthermore, the catheter of the present invention may have a one-layer tube structure or two-layer tube structure.

According to the method for producing a medical long object of the present invention, at least a part of the surface of the medical long object is made of a polymeric material containing a laser color developing agent, and only the part of the surface of the medical long object in which a color is to be developed is irradiated with laser light to allow the laser color developing agent to develop a color, whereby any pattern is formed on the surface of the medical long object.

Hereinafter, the method for producing a medical long object will be specifically described by exemplifying the case where the medical long object of the present invention is a guide wire for an endoscope. It should be noted that the method for producing a medical long object of the present invention is used not to be limited to a guide wire for an endoscope.

(1) First, a laser color developing agent and another additive, if required, are added to a polymeric material, and its mixture is kneaded so that the additives are uniformly dispersed in the material.

(2) Then, a core fiber (e.g., made of a Ni-Ti alloy) is coated with the resultant polymeric material containing a laser color developing agent. The coating method is not particularly limited. For example, extrusion molding, injection molding, insert injection molding, and press molding can be used.

(3) Thereafter, the surface made of the polymeric material containing a laser color developing agent is irradiated with laser light in accordance with the laser color developing agent, thereby allowing the laser color developing agent to develop a color and forming a mark.

FIG. 1 is a conceptual diagram showing an example of a laser light irradiation method in production of the medical long object of the present invention. In FIG. 1, reference numeral 1 denotes a medical long object (guide wire), 2 denotes lasers, and 3 denotes laser light. In FIG. 1, the guide wire 1 moves in an arrow direction between two lasers 2 and is irradiated with the laser light 3.

As shown in FIG. 1, when the guide wire 1 is irradiated with the laser light 3 while the guide wire 1 is being moved, since the laser color developing agent is uniformly present on the surface of the guide wire 1, marking can be conducted at any place and in any shape by regulating an irradiation direction, an irradiation time, and the like. For example, a pattern such as a letter and complicated graphics can be easily formed. FIGS. 2A to 2D show four specific examples of marking. In FIGS. 2A to 2D, reference numeral 4 denotes color developing portions and 5 denotes non-color developing portions. The color developing portions 4 and the non-color developing portions 5 form a pattern.

As shown in FIG. 1, when the laser light 3 is radiated from two directions by using two lasers 2, marking can be also conducted on the periphery of the guide wire 1. Note that the laser irradiation method is not particularly limited to the above.

Although, marking can be conducted at any place on the guide wire in according with its use, in case of the guide wire for an endoscope, it is preferable that the tip end of marking is placed at 1 to 7 centimeters base end side from the tip end of guide wire 1, the base end of marking is placed at 15 to 70 centimeters base end side from the tip end of guide wire 1.

In prescribing place and length of the marking as mentioned above, it gives the following advantage. First of all, by conducting a marking only at a portion at the tip end side of the guide wire, an operator can easily distinguish between the tip end and the base end of guide wire.

Furthermore, in case of the guide wire for an endoscope, various catheters for treatment, such as EST knife, drainage catheter, stent delivery catheter, balloon dilation catheter and like, are operated under observation using an endoscope, with tip end of guide wire projected from the tip end of endoscope by dozens centimeters. The operation that mentioned above includes the operation for replacing a catheter with others. Therefore, in the operation, movement of the guide wire must be observed. By conducting a marking at the projected portion from tip end of the endoscope, the observation can be done easily. A little unevenness may be formed in the marking portion irradiated by laser. By not conducting a marking at the portion of 1–7 cm from the tip end, the tip end maintains its flexibility and delicate sense of inserting motion. Furthermore by not conducting a marking at the portion of 1–7 cm from the tip end, the drawback that the surface coating described below will cover the marking portion and the marking is less visible can be avoided. Furthermore, by conducting a marking at minimum portion as needed, production efficiency should be enhanced and cost should be minimized.

(4) Furthermore, if required, the surface of the guide wire 1 is coated with a hydrophilic polymer. A conventionally known coating method (dipping, etc.) can be used.

It should be noted that unlike the case where a color developing portion is formed by printing with ink, a color developing portion formed with a laser color developing agent is excellent in solvent resistance. Therefore, a mark is not eliminated with a solvent used in coating of the hydrophilic polymer. Furthermore, a time for drying ink (which is necessary in the method of printing with ink) is not required, and coating of a hydrophilic polymer can be conducted immediately after irradiation with laser light.

Furthermore, according to the above-mentioned method, coating of the hydrophilic polymer is conducted after irradiation with laser light. However, it is also possible to conduct irradiation with laser light after coating of the hydrophilic polymer.

It has been conventionally impossible to conduct marking on a medical long object just before or during operation. However, depending upon the use and purpose of the medical long object, it is desired that marking is conducted just before or during operation to specify the position of a lesion, etc. In the medical long object of the present invention, if coating of a hydrophilic polymer is conducted before irradiation with laser light, it is also possible to conduct a marking due to irradiation with laser light which pass through the endoscope on the guide wire which accommodated in the lumen during operation, which is very useful by reason of that the length of lesion become observable and like.

The medical long object of the present invention thus obtained is provided with a mark at least in a part of the surface thereof. Therefore, the movement of the medical long object in an axial direction is recognized, and information on a scale and the like can be displayed, which is useful. Furthermore, as described above, there is no possibility that a mark peels off during use. Furthermore, the medical long object of the present invention does not have a raise or a recess in a mark portion to be formed, and has a smooth surface.

EXAMPLES

Hereinafter, the present invention will be specifically described by way of illustrative examples. It should be noted that the present invention is not limited thereto.

Example 1

First, 0.2 g of Mica composition 1 and 3 g of a blue pigment were added to 99.8 g of polyurethane resin (ether type), and the mixture thus obtained was kneaded so that Mica composition 1 and the blue pigment were uniformly dispersed in the polyurethane resin.

Then, a core wire (made of a Ni-Ti alloy, having a diameter of 0.6 mm) was coated with the resultant resin containing a laser color developing agent by extrusion molding so as to have an outer diameter of 0.8 mm, whereby a guide wire was obtained.

Thereafter, the surface formed of the resin containing a laser color developing agent was irradiated with YAG laser light by a laser light irradiation method shown in FIG. 1, whereby a mark was formed. The movement speed of the guide wire was 300 mm/min., and the energy output of an irradiation origin was 1800 W.

Furthermore, the surface was coated with a maleic anhydride ethyl ester copolymer by dipping, followed by being dried. Thus, a medical long object (guide wire) of the present invention was obtained.

Example 2

A medical long object (guide wire) of the present invention was obtained by the same method as that of Example 1, except that irradiation with laser light was conducted after-coating of a maleic anhydride ethyl ester copolymer in place of conducting coating of a maleic anhydride ethyl ester copolymer after irradiation with laser light.

Example 3

First, 0 to 1 g of Iriodin (laser color developing agent), 30 to 70 g of tungsten, and 0 to 10 g of fluorine powder were added to 30 to 70 g of polyurethane resin respectively, and the mixture thus obtained was kneaded so that these components were uniformly dispersed.

Then, core wires (made of a Ni-Ti alloy) previously tapered were coated with the resultant resin containing a laser color developing agent by extrusion molding so as to have outer diameters respectively shown in Table 1.

Each core wire thus obtained was cut in predetermined length and the core wire was coated (hydrophilic polymer coat portion) with a hydrophilic polymer (a maleic anhydride ester copolymer) to a length shown in Table 1 from a tip end portion by dipping. Thereafter, the surface formed of the resin containing a laser color developing agent was irradiated with YAG laser light by the laser light irradiation method shown in FIG. 1, whereby a mark was formed (visual marker portion). The movement speed of the guide wire was 300 mm/min., and the energy output of an irradiation origin was 1800 W.

Furthermore, the tip end portion was rounded and the remaining portion was coated (hand part silicon coat portion) with silicon by dipping to obtain a medical long object (guide wire). FIGS. 3E and 3F show plan views of medical long objects (guide wires) produced in Example 3. In FIGS. 3E and 3F, reference numeral 4 denotes a color developing portion, 5 denotes a non-color developing portion, 6 denotes a visual marker portion, 7 denotes a hydrophilic polymer coat portion, and 8 denotes a hand part silicon coat portion.

Table 1 shows the size and the like of each portion of the guide wires produced in Example 3.

TABLE 1

| Example | Guide wire outer diameter mm (inch) | Guide wire length cm | Hydrophilic polymer coat portion length cm | Laser treatment length cm | Laser treatment shape |
|---|---|---|---|---|---|
| 3-1 | 0.635 (0.025) | 260 | 5 | 10 | E |
| | 0.635 (0.025) | 260 | 50 | 20 | E |
| | 0.635 (0.025) | 260 | 100 | 30 | E |
| 3-2 | 0.635 (0.025) | 450 | 5 | 10 | E |
| | 0.635 (0.025) | 450 | 50 | 20 | E |
| | 0.635 (0.025) | 450 | 100 | 30 | E |
| 3-3 | 0.889 (0.035) | 260 | 5 | 10 | F |
| | 0.889 (0.035) | 260 | 50 | 20 | F |
| | 0.889 (0.035) | 260 | 100 | 30 | F |
| 3-4 | 0.889 (0.035) | 450 | 5 | 10 | F |
| | 0.889 (0.035) | 450 | 50 | 20 | F |
| | 0.889 (0.035) | 450 | 100 | 30 | F |

The guide wires of the present invention obtained in Examples 1 to 3 had marks with a desired shape at a desired position, whereby the movement of the guide wires in an axial direction was able to be recognized during such as insertion. Furthermore, marks did not peel off during use. Furthermore, the guide wires of the present invention had a smooth surface (cylindrical surface), and a raise and a recess were not present in the mark portions.

Unlike the case of printing with ink, marks were not eliminated with a solvent used for coating of the hydrophilic polymer. Furthermore, it was possible to conduct coating of the hydrophilic polymer immediately after irradiation with laser light (Example 1).

Furthermore, by optimizing place and length of marking, it is possible that work efficiency of operator and production efficiency should be enhanced.

The medical long object of the present invention is provided with marks at least in a part of the surface thereof, so that the movement of the medical long object in an axial direction is recognized. Furthermore, information on a scale and the like can be displayed, so that the medical long object of the present invention is useful. Furthermore, the medical long object of the present invention has no problems that have not been conventionally solved.

According to the method for producing a medical long object of the present invention, the medical long object of the present invention can be preferably produced.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a medical long object, comprising:

forming at least a part of a surface of a medical long object with a polymeric material containing a laser color developing agent;

irradiating only a portion of the surface of the medical long object in which a color is to be developed with laser light so as to allow the laser color developing agent to develop a color, thereby forming any pattern on the surface of the medical long object and also forming unevenness on the surface of the medical long object; and coating a hydrophilic polymer on the part of the surface of the medical long object which includes the unevenness.

2. A method for producing a medical long object according to claim 1, wherein the laser color developing agent is contained 0.01 to 10% by mass on the total amount of the polymeric material component.

3. A method for producing a medical long object, comprising:

forming at least a part of a surface of a medical long object with a polymeric material containing a laser color developing agent;

coating a hydrophilic polymer on the part of the surface; and irradiating only a portion of the surface of the medical long object in which a color is to be developed with laser light to allow the laser color developing agent to develop a color, thereby forming a pattern on the surface of the medical long object, the irradiating with laser light occurring after the part of the surface is coated with the hydrophilic polymer.

* * * * *